United States Patent [19]

Hitzel et al.

[11] 4,158,063

[45] Jun. 12, 1979

[54] ACYLAMINO(ALKYL)BENZENE DERIVATIVES AND PROCESS FOR PREPARING THEM

[75] Inventors: Volker Hitzel, Hofheim; Rudi Weyer, Kelkheim; Elmar Bosies, Heppenheim, all of Fed. Rep. of Germany

[73] Assignee: Hoechst Aktiengesellschaft, Frankfurt am Main, Fed. Rep. of Germany

[21] Appl. No.: 757,290

[22] Filed: Jan. 6, 1977

[30] Foreign Application Priority Data

Jan. 8, 1976 [DE] Fed. Rep. of Germany ....... 2600513

[51] Int. Cl.$^2$ ............................................ A61K 31/165
[52] U.S. Cl. ................................. 424/324; 260/558 A;
260/558 D; 260/558 P; 260/559 A; 260/559 S
[58] Field of Search ........... 260/558 A, 558 D, 558 P, 260/559 A, 559 S; 424/324

[56] References Cited

U.S. PATENT DOCUMENTS

| 3,549,689 | 12/1970 | Frey et al. ........................ 260/471 |
| 3,706,796 | 12/1972 | Blake ............................... 260/558 D |
| 4,044,147 | 8/1977 | Nelson ............................. 260/558 A |

FOREIGN PATENT DOCUMENTS

| 46-18508 | 9/1966 | Japan ............................. 424/324 |
| 48-23898 | 12/1966 | Japan ............................. 424/324 |

Primary Examiner—Frederick E. Waddell
Attorney, Agent, or Firm—Curtis, Morris & Safford

[57] ABSTRACT

The invention relates to acylamino(alkyl)benzene derivatives of the general formula

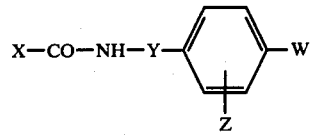

in which
W represents a group which can be converted into a carboxyl group, or an aldehyde group or an oxymethyl group or their derivatives or also a low molecular weight alkyl group, preferably a methyl group,
X represents an aromatic or hetero-aromatic ring system,
Y represents a single chemical bond or a hydrocarbon bridge, and
Z represents hydrogen or one or even several other substituents,
to their preparation and to pharmaceutical compositions containing them. The compounds have blood sugar lowering activity and may be used in the therapy of diabetes mellitus.

7 Claims, No Drawings

ACYLAMINO(ALKYL)BENZENE DERIVATIVES AND PROCESS FOR PREPARING THEM

The present invention relates to acylamino-(alkyl)-benzene derivatives having blood sugar lowering action.

It is known that sulfonamide derivatives such as sulfonylureas, sulfonylsemicarbazides, sulfonamidopyrimidines as well as some other sulfonamide heterocycles and sulfonyl urethanes have a blood sugar lowering action on not pre-treated test animals. Some of these compounds are largely used in human therapy for the treatment of diabetes mellitus. Now, it has been found that, surprisingly, also acylamino(alkyl)-benzene derivatives provoke a lowering of the blood sugar level.

Thus, the present invention provides acylamino(alkyl)-benzene derivatives having blood sugar lowering action, in particular compounds of the general formula I

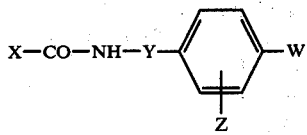

in which
  W represents a group which can be converted into a carboxyl group, or an aldehyde group or an oxymethyl group or their derivatives or also a low molecular weight alkyl group, preferably a methyl group,
  X represents an aromatic or hetero-aromatic ring system,
  Y represents a single chemical bond or a hydrocarbon bridge, and
  Z represents hydrogen or one or even several other substituents.

As derivatives of the compounds which carry an aldehyde or oxymethyl group, there may be mentioned, for example, an acetal or an oxime or also an ester which contains the oxymethyl compound as the alcohol component.

As the substituent X in the above formula, there may be used in the first instance mono-nucleic aromatic or heteroaromatic ring systems, in particular the unsubstituted or mono-substituted or poly-substituted phenyl radical, the pyridine radical or the thiophen radical.

In the same manner, polynucleic aromatic or heteroaromatic ring systems may be used, among them also those which are partially hydrogenated, for example naphthalene, benzofuran, dihydrobenzofurane, chromane, chromene or homochromane, quinoline and benzothiophen.

As the member Y in the above formula, there may be used in addition to a single chemical bond above all low molecular weight hydrocarbon chains. These may be straight chain and branched hydrocarbons and also be substituted or interrupted by a heteroatom.

The member Z is in the first instance hydrogen, but a substitution of the central phenyl nucleus by one or several substituents is also possible.

In the tests for the activity of the compounds, especially the compounds of the formula II have been found to have an outstanding activity.

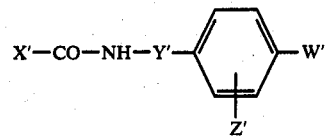

In this formula
  W' represents an aldehyde or oxymethyl group or the derivatives thereof or a low molecular weight alkyl group, preferably a methyl group,
  X' represents
  (a) a phenyl radical which may carry at any desired position the substituents R, $R_1$ and $R_2$, R being hydrogen, alkyl, alkoxy, alkenoxy, alkoxy-alkoxy, phenoxy, halogen, amino, alkylamino, anilino or trifluoromethyl, and $R_1$ and $R_2$ represent, independently of one another, hydrogen, alkyl, alkoxy or halogen;
  (b) ring systems of the formula III

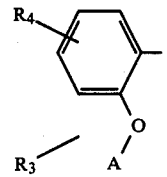

in which $R_3$ represents hydrogen or methyl and $R_4$ represents hydrogen, alkyl, alkoxy or halogen in m- or p-position to the CONH group and A represents a hydrocarbon chain of 2 to 4 carbon atoms;
  (c) a quinoline radical of the formula IV

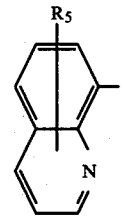

in which R represents hydrogen, methyl, methoxy or halogen, or
  (d) a thiophen radical of the formula V

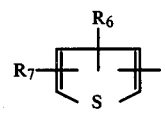

in which $R_6$ and $R_7$, independently of one another, each represent hydrogen, alkyl, alkoxy or halogen; or
  (e) a pyridine radical of the formula VI

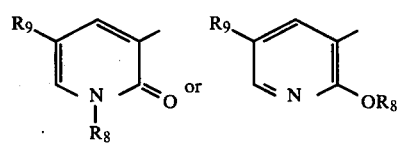

in which $R_8$ represents alkyl and $R_9$ represents halogen, preferably chlorine and bromine, Y' represents a simple chemical bond or a hydrocarbon radical of 1 to 3 carbon atoms, Z' represents hydrogen, halogen, alkyl or alkoxy.

Alkyl or alkenyl as well as the alkyl moieties in alkoxy, alkenoxy, alkoxyalkoxy and alkylamino in the sense of the above definitions are straight chain or branched hydrocarbon radical with not too great a number of carbon atoms.

It has been found that those members that have up to 6 carbon atoms have the best activity.

Halogen in the above definitions is, in the first instance chlorine and bromine, but, especially in the case that X' is a phenyl radical, also fluorine.

The corresponding iodine compounds are generally likewise active, but their administration is less recommandable.

Preferred bridge members Y are hydrocarbon bridges with 2 carbon atoms, which themselves may be substituted, even by alkyl groups. Accordingly, the group —$CH_2$—$CH_2$— and the group —$CH(CH_3)$—$CH_2$— are particularly preferred. Less preferred are the other straight chain or branched hydrocarbon bridges having up to 3 carbon atoms.

Furthermore, the invention provides a process for preparing the afore-mentioned compounds. This process comprises (a) reacting an amino compound of the general formula

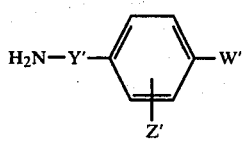

with a reactive derivative of the acid X'COOH, (b) oxidizing a compound of the general formula

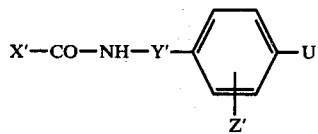

in which U is a hydroxymethyl group, (c) reducing a compound of the general formula

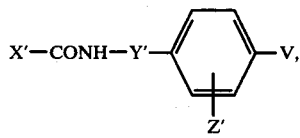

in which V is a carboxyl- or carboxylic acid ester or an aldehyde group, (d) in a compound of the general formula

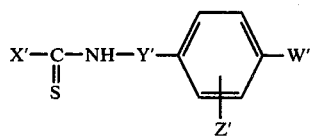

replacing the sulfur by an oxygen atom, or (e) in a compound of the general formula

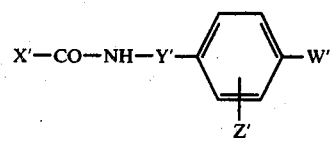

alkylating a hydroxy group standing for Z' or being present in the radical X', and, if desired, converting the compound so obtained into a derivative such as an acetal, oxime or ester.

The amino compounds serving as starting substances according to the process variant (a) are known or may be prepared without difficulty by processes known for analogous compounds.

These amino compounds or the salts thereof are reacted, preferably in the presence of bases, with reactive derivatives of the acid X'-COOH, for example their halides, anhydrides, mixed anhydrides, azides or esters.

The starting substances used for the process variant (b) may be obtained by acylating an amine of the general formula

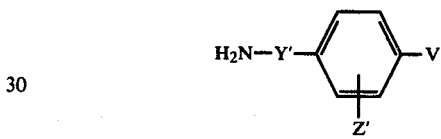

or a salt thereof with the radical X'CO— or, for example, reducing a compound of the general formula

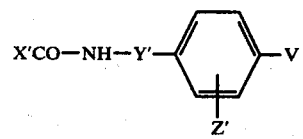

and, if desired, subsequently oxidizing the resulting compound.

Depending on the nature of the group V, they may be converted by suitable reactions into the compounds of the invention. Such suitable reactions may consist in, for example a reduction if the substituent V is a carboxylic acid or a carboxylic acid ester.

An oxidative conversion is effected, for example, if V represents an oxymethyl grouping.

The starting substances for the process variant (c) are obtained by reacting, for example an amino compound of the formula

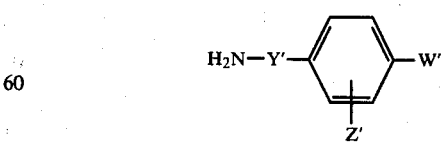

or an ester or salt thereof with the reactive derivative of a thiocarboxylic acid X'CSOH.

These thioamides may be desulfurized according to known methods used for similar compounds, especially those of the series of sulfonyl ureas, the treatment with hydrogen peroxide or sodium peroxide being particularly suitable.

The desulfurization may also be effected over an isothiourea ether.

The etherification of the hydroxy groups according to process variant (d) is carried out according to known methods, for example by the reaction with dialkyl sulfate or alkyl- or aralkyl halide.

The compounds of the invention have a blood sugar lowering activity. This activity can be determined by administering the compounds in doses of 10 to 400 mg, preferably about 100 mg/kg to normally fed rabbits and determining the blood sugar level over a prolonged period of time according to the known method of Hagedorn-Jensen or with an autoanalyzer.

The compounds of the invention are intended to be used preferably for the manufacture of orally administrable compositions with blood sugar lowering activity for the treatment of diabetes mellitus and may be administered as such or, optionally, in the form of their salts or esters or in the presence of substances which lead to a salt formation.

The medicinal compositions are preferably tablets which contain, in addition to the products of the invention the usual carrier and auxiliary substances such as talcum, starch, lactose, tragacanth or magnesium stearate.

A pharmaceutical composition which contains the described compounds as active substance, for example a tablet or a powder, with or without addition, is advantageously brought into a suitable dosage unit form. The dose is then to be adapted to the activity of the active substance and to the desired effect. Suitably, the dose per unit is about 0.1 to 2, preferably 0.5 to 1 g, but lower or higher dosage units may also be used which may be divided or multiplied before administration.

The acylamino(alkyl)-benzene derivatives of the invention may be used alone in the treatment of diabetes mellitus or in combination with other orally administrable antidiabetics. As such not only blood sugar lowering sulfonyl ureas, but also compounds of different chemical structure, such, for example, as biguanides, in particular the phenylethyl-biguanide or the dimethyl-biguanide.

The following examples illustrate some of the numerous process variants which may be applied for the synthesis of the compounds of the invention, but they are not intended to limit the scope of the invention.

EXAMPLE 1

5-Chloro-2-methoxy-N-(2-<4-methylphenyl>-ethyl)-benzamide

A solution of 20.4 g of 5-chloro-2-methoxy-benzoyl chloride in 50 ml of toluene was added dropwise, while stirring and slightly cooling to a solution of 13.5 g of 2-(4-methylphenyl)-ethylamine and 10.1 g of triethylamine in 150 ml of anhydrous toluene. The whole was then heated for 2 hours to 80°-90° C. After having washed the reaction mixture with water, dilute hydrochloric acid and a solution of sodium bicarbonate, the toluene phase was dried over sodium sulfate and concentrated under reduced pressure. The residue was recrystallized from petroleum ether (B.p. 60°-90° C.). The 5-chloro-2-methoxy-N-(2-<4-methylphenyl>-ethyl)-benzamide was found to melt at 77°-78° C.

In analogous manner, there were obtained by the reaction of 2-(4-methylphenyl)-ethylamine with the corresponding acid chlorides the following compounds:
2-Ethoxy-5-chloro-N-(2-<4-methylphenyl>-ethyl)-benzamide, M.p. 94°-95° C. (from ethanol).
2-Allyloxy-5-chloro-N-(2-<4-methylphenyl>-ethyl)-benzamide, M.p. 55° C. (triturated with di-isopropyl ether).
3,5-Dichloro-N-(2-<4-methylphenyl>-ethyl)-benzamide, M.p. 123° C. (from di-isopropyl ether).
2-Amyloxy-5-chloro-N-(2-<4-methylphenyl>-ethyl)-benzamide, M.p. 72° C. (from ethanol).
2-Butoxy-5-chloro-N-(2-<4-methylphenyl>-ethyl)-benzamide, M.p. 64° C. (from ethanol).
2-Methoxy-5-methyl-N-(2-<4-methylphenyl>-ethyl)-benzamide, M.p. 64°-66° C. (from di-isopropyl ether).
4-Chloro-N-(2-<4-methylphenyl>-ethyl)-benzamide, M.p. 155° C. (from ethyl acetate).
3-Chloro-N-(2-<4-methylphenyl>-ethyl)-benzamide, M.p. 94° C. (from di-isopropyl ether).
5-Chloro-2-methoxyethoxy-N-(2-<4-methylphenyl>-ethyl)-benzamide, M.p. 84°-86° C. (from ethanol).
5-Chloro-3-methoxy-N-(2-<4-methylphenyl>-ethyl)-thiophene-2-carboxylic acid amide, M.p. 88°-89° C. (from di-isopropyl ether).

In analogous manner, there were obtained from 2-(3,4-dimethylphenyl)-ethylamine with the corresponding acid chlorides:
5-Chloro-2-methoxy-N-(2-<3,4-dimethylphenyl>-ethyl)-benzamide, M.p. 72°-74° C. (triturated with petroleum ether).
2-Butoxy-5-chloro-N-(2-<3,4-dimethylphenyl>-ethyl)-benzamide, M.p. 56°-58° C. (triturated with petroleum ether).

In analogous manner, there was obtained from 2-(4-ethylphenyl)-ethylamine wtih 2-butoxy-5-chloro-benzoyl chloride:
2-Butoxy-5-chloro-N-(2-<4-ethylphenyl>-ethyl)-benzamide, M.p. 72°-74° C. (triturated with petroleum ether).

In analogous manner, there were obtained from 4-methylaniline and the corresponding acid chlorides:
5-Chloro-2-methoxy-N-(4-methylphenyl)-benzamide, M.p. 153° C. (from ethanol).
2-Ethoxy-5-chloro-N-(4-methylphenyl)-benzamide, M.p. 158° C. (from ethanol).

In analogous manner, there was obtained from 1-(4-methylphenyl)-ethylamine and 5-chloro-2-methoxy-benzoyl chloride:
5-Chloro-2-methoxy-N-(1-<4-methylphenyl>-ethyl)-benzamide, M.p. 123°-125° C. (from dilute methanol).

In analogous manner, there was obtained from 4-methylbenzylamine and 5-chloro-2-methoxy-benzoyl chloride:
5-Chloro-2-methoxy-N-(4-methylbenzyl)-benzamide, M.p. 115°-117° C. (from dilute methanol).

EXAMPLE 2

5-Chloro-2-methoxy-N-(2-<4-ethylphenyl>-ethyl)-benzamide

A solution of 4.1 g of 5-chloro-2-methoxy-benzoyl chloride in 20 ml of toluene was added dropwise to a suspension of 4.65 g of 2-(4-ethylphenyl)-ethylamine hydrochloride in 100 ml of anhydrous toluene after addition of 5 ml of pyridine. The whole was heated under reflux, then shaken with water, dilute hydrochloric acid and a solution of sodium bicarbonate and dried over sodium sulfate. After concentration under reduced pressure, the residue, which solidified only slowly, was filtered off with suction after addition of petroleum ether (B.p. 30°–60° C.). The 5-chloro-2-methoxy-N-(2-<4-ethylphenyl>-ethyl)-benzamide so obtained was found to melt at 66°–68° C.

In analogous manner, there was obtained by the reaction of 2-(4-ethylphenyl)-ethylamine . hydrochloride with 6-chlorochromane-8-carboxylic acid chloride:

6-Chloro-N-(2-<4-ethylphenyl>-ethyl)-chromane-8-carboxylic acid amide, M.p. 58°–59° C. (triturated with petroleum ether).

EXAMPLE 3

5-Chloro-2-methoxy-N-(2-<4-hydroxymethylphenyl>-ethyl)-benzamide

A solution of 20.4 g of 5-chloro-2-methoxy-benzoyl chloride in 150 ml of methylene chloride was added at 0° C. to a suspension of 15 g of 4-(2-aminoethyl)-benzyl alcohol in 90 ml of 1 N-sodium hydroxide solution. The whole was stirred for 3 hours at room temperature, filtered off with suction, the phases were separated, the organic phase was washed with dilute hydrochloric acid, dried over sodium sulfate and concentrated. The oil obtained was dissolved in trichloroethylene and brought to crystallization by addition of ligroine and ether. The 5-chloro-2-methoxy-N-(2-<4-hydroxymethylphenyl>-ethyl)-benzamide was found to melt at 80°–82° C.

The 4-(2-aminoethyl)-benzyl alcohol used as the starting material was prepared in the following manner:

4-(2-Acetamido-ethyl)-benzoic acid was hydrolyzed to give thee 4-(2-amino-ethyl)-benzoic acid hydrochloride (M.p. 306°–307° C.), then reacted to the corresponding ethyl ester hydrochloride (M.p. 250° C.) and its free amino compound was reduced with lithium-aluminium hydride to give the 4-(2-aminoethyl)-benzyl alcohol (oil).

EXAMPLE 4

5-Chloro-2-methoxy-N-(2-<4-hydroxymethylphenyl>-ethyl)-benzamide 5.43 g of 4-(2-<5-chloro-2-methoxy-benzamido>-ethyl)-benzoic acid ethyl ester were heated under reflux for 3 hours with 1 g of lithium-aluminium hydride in 150 ml of absolute ether. After decomposition with water and 2 N-sodium hydroxide solution, the whole was filtered with suction, the ether solution was dried, concentrated and the oily residue was dissolved in trichloroethylene. After addition of ligroine and ether the product precipitated. The 5-chloro-2-methoxy-N-(2-<4-hydroxymethylphenyl>-ethyl)-benzamide was found to melt at 80°–82° C.

The ethyl ester (M.p. 73°–76° C.) used as the starting substance was prepared from 4-(2-<5-chloro-2-methoxy-benzamido>-ethyl)-benzoic acid.

In analogous manner, there was obtained by the reduction of the 4-(2-<5-chloro-2-methoxy-benzamido>-ethyl)-2-methoxy-benzoic acid ethyl ester (M.p. 75°–76° C.):

5-Chloro-2-methoxy-N-(2-<4-hydroxymethyl-3-methoxy-phenyl>-ethyl)-benzamide, M.p. 145°–146° C. (from ethyl acetate).

In analogous manner, there was obtained by the reduction of the 4-(2-<5-chloro-2-methoxy-benzamido>-propyl)-benzoic acid ethyl ester (M.p. 66°–67° C.):

5-Chloro-2-methoxy-N-(2-<4-hydroxymethylphenyl>-propyl)-benzamide, M.p. 65°–67° C. (from diisopropyl ether).

In analogous manner, there was obtained by reduction of 4-(2-<5-chloro-2-methoxy-benzamido>-ethyl)-2-ethoxy-benzoic acid (M.p. 115°–117° C.):

5-Chloro-2-methoxy-N-(2-<3-ethoxy-4-hydroxymethylphenyl>-ethyl)-benzamide, M.p. 127°–128° C. (from nitromethane).

EXAMPLE 5

5-Chloro-2-methoxy-N-(2-<4-formylphenyl>-ethyl)-benzamide

A solution of 20.8 g of 5-chloro-2-methoxy-benzoyl chloride in 90 ml of methylene chloride was added, while stirring, to 26 g of 4-(2-aminoethyl)-benzaldehyde-diethylacetal-hydrochloride in 50 ml of 2 N-sodium hydroxide solution. Then, further 50 ml of 2 N-sodium hydroxide solution were added, after 1 hour the whole was filtered with suction, the phases were separated and the aqueous layer was extracted with ether. The combined organic phases were dried and concentrated. The residue was triturated with 2 N-hydrochloric acid, filtered with suction and recrystallized from toluene/ligroine. The 5-chloro-2-methoxy-N-(2-<4-formylphenyl>-ethyl)-benzamide was found to melt at 115°–116° C.

The acetal used as the starting material was prepared in the following manner:

4-(2-acetamido-ethyl)-benzoic acid was reduced over the mixed anhydride with sodium-boron hydride to the acetic acid-N-(2-<4-hydroxymethylphenyl>-ethyl)-amide (m.p. 70°–72° C.) and then oxidized with activated manganese dioxide to give the acetic acid-N-(2-<4-formylphenyl>-ethyl)-amide (M.p. 78°–80° C.). The following acid hydrolysis gave the 4-(2-aminoethyl)-benzaldehyde-hydrochloride (M.p. >330° C.), which was then reacted to yield the above used acetal (M.p. >320° C.).

EXAMPLE 6

5-Chloro-2-methoxy-N-(2-<4-formylphenyl>-ethyl)-benzamide 3 g of 5-chloro-2-methoxy-N-(2-<4-hydroxymethylphenyl>-ethyl)-benzamide (prepared according to Examples 3 and 4, respectively, were dissolved in 100 ml of methylene chloride. After the addition of 5 g of activated manganese dioxide, the whole was stirred for 1 day, 2.5 g of manganese dioxide were added again and after a further day the whole was suction-filtered. The methylene chloride was concentrated and the residue was recrystallized from toluene/ligroine. The 5-chloro-2-methoxy-N-(2-<4-formylphenyl>-ethyl)-benzamide so prepared was found to melt at 115°–116° C.

In analogous manner, there was obtained from 5-chloro-2-methoxy-N-(2-<4-hydroxymethyl-3-methoxy-phenyl>-ethyl)-benzamide:

5-Chloro-2-methoxy-N-(2-<4-formyl-3-methoxy-phenyl>-ethyl)-benzamide. M.p. 133°–134° C. (from toluene).

In analogous manner, there was obtained from 5-chloro-2-methoxy-N-(2-<4-hydroxymethyl-phenyl>-propyl)-benzamide:

5-Chloro-2-methoxy-N-(2-<4-formyl-phenyl>-propyl)-benzamide.

In analogous manner, there was obtained from 5-chloro-2-methoxy-N-(2-<3-ethoxy-4-hydroxymethylphenyl>-ethyl)-benzamide:
5-Chloro-2-methoxy-N-(2-<3-ethoxy-4-formylphenyl>-ethyl)-benzamide, M.p. 100°–102° C. (from di-isopropyl ether).

EXAMPLE 7

2-Acetamino-5-chloro-N-(2-<4-methylphenyl>-ethyl)-benzamide

A.

2-Amino-5-chloro-N-(2-<4-methylphenyl>-ethyl)-benzamide 7.3 g of isatoic acid anhydride were heated in 50 ml of anhydrous dimethylformamide to 80° C. and then combined dropwise with 5 g of 2-(4-methylphenyl)-ethylamine. The whole was stirred for 5 hours at 80°–90° C., poured in 300 ml of water, filtered off with suction and the 2-amino-5-chloro-N-(2-<4-methylphenyl>-ethyl)-benzamide was recrystallized from ethanol.
It was found to melt at 126° C.

B.

2-Acetamino-5-chloro-N-(2-<4-methylphenyl>-ethyl)-benzamide 4.3 g of 2-amino-5-chloro-N-(2-<4-methylphenyl>-ethyl)-benzamide were heated for 3 hours under reflux in 100 ml of toluene after addition of 2 ml of triethylamine and 1.2 ml of acetyl chloride. After having allowed the whole to cool, it was shaken with water. The 2-acetamino-5-chloro-N-(2-<4-methylphenyl>-ethyl)-benzamide which during this time already crystallized from the toluene phase was filtered off with suction and, after recrystallization from ethanol, it was found to melt at 149° C.

In a manner analogous to that described in Example 7A., there was obtained from N-ethyl-5-chloro-isatoic acid anhydride and 2-(4-methylphenyl)-ethylamine:
2-Ethylamino-5-chloro-N-(2-<4-methylphenyl>-ethyl)-benzamide, M.p. 126° C. (from ethanol).

EXAMPLE 8

5-Chloro-2-methoxy-N-(2-<4-methylphenyl>-ethyl)-benzamide 10 g of 5-chloro-2-methoxy-benzoic acid methyl ester and 7 g of 2-(4-methylphenyl)-ethylamine were heated for 6 hours in to 145° C. in 5 ml of xylene. During that time, the methanol which was forming was distilled off. After having allowed the whole to cool it was dissolved in ethyl acetate, shaken with dilute hydrochloric acid, the organic phase was dried and concentrated under reduced pressure. The residue was recrystallized from petroleum ether (B.p. 60°–90° C.). The 5-chloro-2-methoxy-N-(2-<4-methylphenyl>-ethyl)-benzamide was found to melt at 77°–78° C.

EXAMPLE 9

6-Chloro-N-(2-<4-methylphenyl>-ethyl)-quinoline-8-carboxylic acid amide 5.2 g of 6-chloro-quinoline-8-carboxylic acid in 150 ml of acetone were combined, while stirring and cooling with ice, with 2.8 g of triethylamine and 2.6 g of chloroformic acid methyl ester. The whole was stirred for about 10 minutes, a solution of 3.4 g of 2-(4-methylphenyl)-ethylamine in 50 ml of 2-(4-methylphenyl)-ethyl-amine in 50 ml of acetone was added and the mixture was again stirred for 1 hour at room temperature. Then, water was added, the precipitate was filtered off with suction, treated with a dilute ammonia solution, undissolved matter was filtered off and recrystallized from dilute methanol. The 6-chloro-N-(2-<4-methylphenyl>-ethyl)-quinoline-8-carboxylic acid amide so obtained was found to melt at 102°–104° C.

In analogous manner, there were obtained by the reaction of 2-(4-methylphenyl)-ethylamine with the corresponding carboxylic acids:
6-Chloro-N-(2-<4-methylphenyl>-ethyl)-chromane-8-carboxylic acid amide, M.p. 97°–99° C. (from dilute methanol).
5-Chloro-2-methoxy-N-(2-<4-methylphenyl>-ethyl)-nicotinic acid amide, M.p. 46°–48° C. (from di-isopropyl ether).
1-Butyl-N-(2-<4-methylphenyl>-ethyl)-pyridone(2)-3-carboxylic acid amide, M.p. 82°–83.5° C. (from petroleum ether).

In analogous manner, there was obtained by the reaction of 1-(4-methylphenyl)-ethylamine with 6-chloro-quinoline-8-carboxylic acid:
6-Chloro-quinoline-N-(1-<4-methylphenyl>-ethyl)-quinoline-8-carboxylic acid amide. M.p. 98°–101° C. (from dilute methanol).

In analogous manner, there was obtained by the reaction of 4-methyl-benzylamine and 5-chloro-2-methyl-benzo[b]-furan-7-carboxylic acid:
5-Chloro-2-methyl-N-(4-methylbenzyl)-benzo[b]furan-7-carboxylic acid amide. M.p. 130°–132° C. (from dilute methanol).

We claim:
1. A pharmaceutical composition useful in the treatment of diabetes mellitus consisting essentially of an inert carrier and a hypoglycemically effective amount of a compound of the general formula:

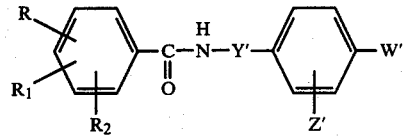

wherein
R is H, alkyl, alkoxy, alkenoxy, alkoxy-alkoxy, phenoxy, halogen, amino, alkylamino, anilino or $CF_3$,
$R_1$, $R_2$ and $Z'$ are independently hydrogen, alkyl, alkoxy or halogen,
W' is an aldehyde group, a hydroxymethyl group or lower alkyl and Y' is selected from —$CH_2$—$CH_2$— and —$CH(CH_3)$—$CH_2$—.

2. The method of treating diabetes mellitus in a patient requiring such treatment which comprises administering to said patient a hypoglycemically effective amount of a compound of the general formula:

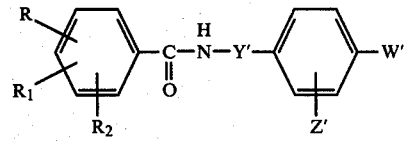

wherein
R is H, alkyl, alkoxy, alkenoxy, alkoxy-alkoxy, phenoxy, halogen, amino, alkylamino, anilino or $CF_3$, $R_1$, $R_2$ and $Z'$ are independently hydrogen, alkyl, alkoxy or halogen, W' is an aldehyde group, a hydroxymethyl group or lower alkyl and Y' is a hydrocarbon group of 1 to 3 carbons.

3. An acylamino(alkyl)benzene derivative of the formula:

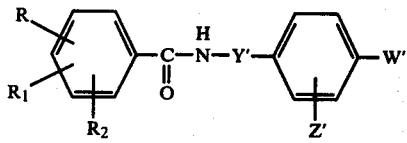

wherein R is H, alkyl, alkoxy, alkenoxy, alkoxy-alkoxy, phenoxy, halogen, amino, alkylamino, anilino or $CF_3$, $R_1$, $R_2$ and $Z'$ are independently hydrogen, alkyl, alkoxy or halogen, W' is an aldehyde group, a hydroxymethyl group or lower alkyl and Y' is selected from $-CH_2-CH_2-$ and $-CH(CH_3)-CH_2-$.

4. An acylamino(alkyl)benzene derivative of the formula:

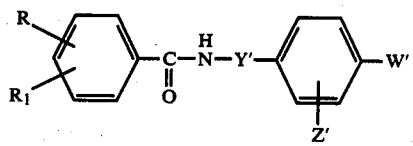

wherein

R is alkyl, alkoxy, alkoxy-alkoxy, alkylamino or acylamino,

R is hydrogen or halogen,

W' is an aldehyde group, a hydroxymethyl group or lower alkyl,

Y' is hydrocarbon of 1 to 3 carbons, and

Z' is hydrogen, lower alkyl or lower alkoxy.

5. 5-Chloro-2-methoxy-N-(2-<4-methylphenyl>-ethyl)-benzamide.

6. 5-Chloro-2-methoxy-N-(2-<4-hydroxymethylphenyl>-ethyl)-benzamide.

7. 5-Chloro-2-methoxy-N-(2-<4-formylphenyl>-ethyl)-benzamide.

* * * * *